US00PP08558P

United States Patent [19]

Reuter

[11] Patent Number: Plant 8,558

[45] Date of Patent: Jan. 25, 1994

[54] PEACH TREE LAUROL

[75] Inventor: Donald Reuter, Richwood, N.J.

[73] Assignee: New Jersey Peach Council, Inc., Clayton, N.J.

[21] Appl. No.: 23,204

[22] Filed: Feb. 22, 1993

[51] Int. Cl.[5] ..... A01H 5/00
[52] U.S. Cl. ..... Plt./43.2
[58] Field of Search ..... Plt. 43.2

*Primary Examiner*—James R. Feyrer

[57] ABSTRACT

A new and distinct peach variety which originated as a mutation of the variety "Jerseyqueen." This new variety is a very late maturing yellow freestone peach which bears large to very large globose to slightly ovate fruit having an attractive bright orange red skin color (as illustrated). The fruit flesh is golden yellow in color, very firm, and slow softening with a very good flavor. The fruit buds are moderately hardy similar to Jerseyqueen with moderate tolerance to *Xanthamonas pruni* bacterial spot.

1 Drawing Sheet

SUMMARY OF THE INVENTION

Origin: This new and distinct variety of peach tree was discovered by me in 1981 growing in a Jerseyqueen tree. The tree wherein the mutation occurred, was in my orchard (Block 19, Lot QF) Harrison Township, Richwood, N.J., USA. I was attracted to the new variety because of its attractive orange red color, very large size and firm flesh in a peach ripening very late in the growing season in New Jersey.

Asexual reproduction of the new variety: Asexual reproduction by budding began in 1982 on Lovell peach seedling rootstock. Second and third generation trees have been propagated for me in 1983 and 1984 and are now in full production. The step of asexual reproduction was performed in my orchard in Harrison Township, Richwood, N.J.

Asexual propagations have demonstrated that the new and unique characteristics of this variety comes true to form and is transmitted through succeeding generations.

Summary of the variety: This new peach variety has a large, vigorous, spreading, growth habit and is a moderately hardy and regular producer of very late maturing, large to very large, golden yellow fleshed fruit with very good flavor and eating quality. The flesh is very firm, slow softening and melting. The fruit is further characterized by having a bright orange red skin color similar to its parent Jerseyqueen (non patented). It ripens 14 days later than Jerseyqueen (non Patented) and 7 days later than Rio Oso Gem (U.S. Plant Pat. No. 84) Autumnglo (non patented) and Encore (U.S. Plant Pat. No. 4,572) the major varieties in the season preceding it. It has more tolerance of bacterial spot (*Xanthamonas pruni*) than Jerseyqueen, Rio Oso Gem and Autumnglo, and equal to Encore in tolerance. No important variety exists for close comparison in this very late season.

BRIEF DESCRIPTION OF THE PHOTOGRAPHS

The accompanying photographic illustrations show typical specimens of the fruit and foliage.

Figure 1:
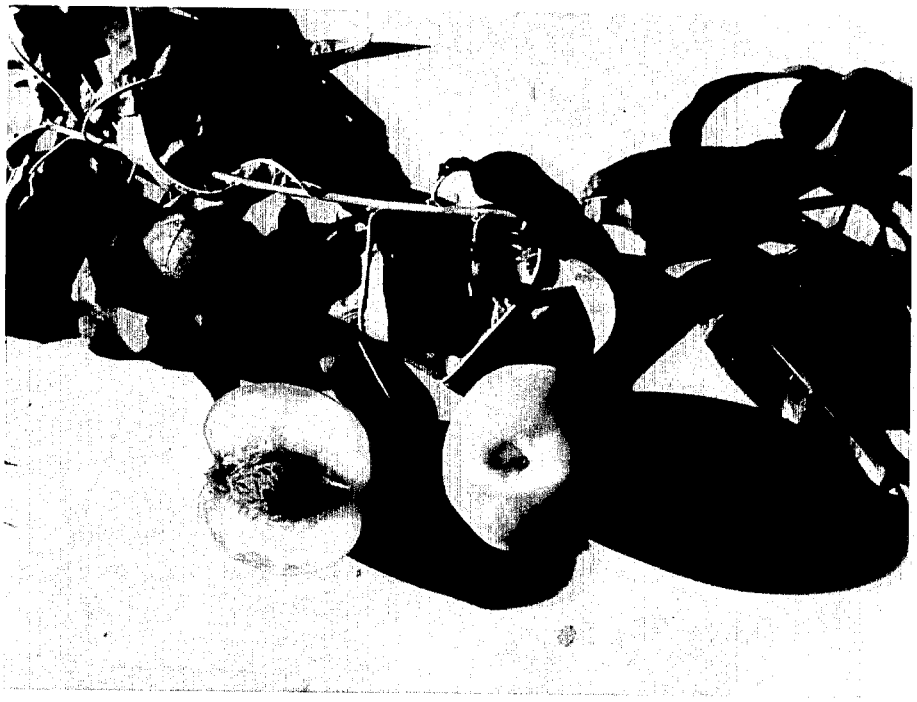
FIG. 1 shows a view of the fruit variety of a whole specimen and a large individual cross section of fruit with seed, at firm melting maturity. Leaves shown are the upper and lower surface of healthy green leaves with leaf buds and glands.
Figure 2:
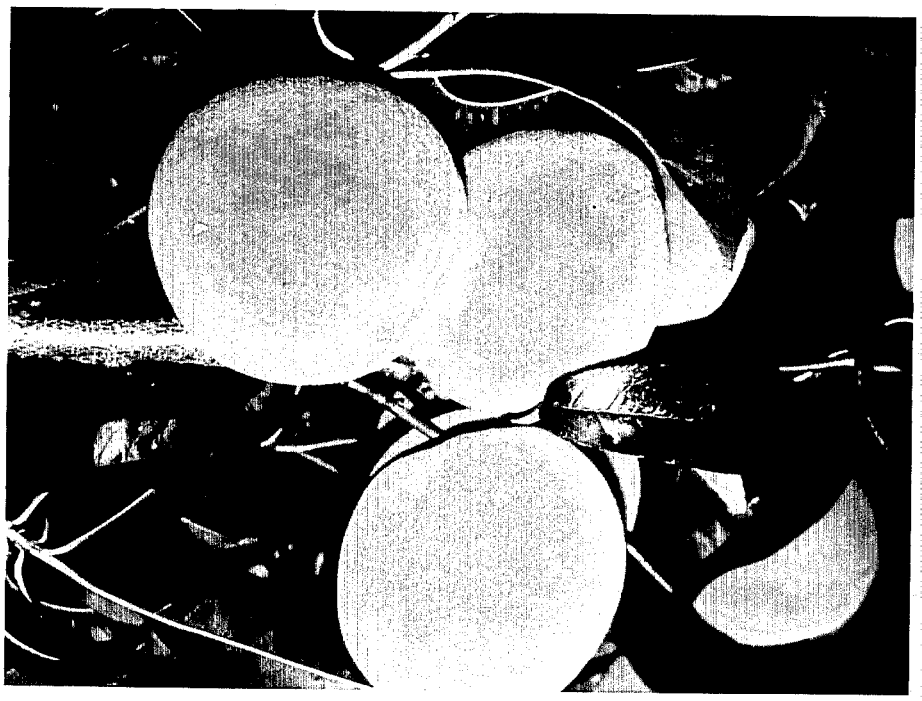
FIG. 2 shows ripe fruit specimens on the tree with color typical of the bright orange red color in the description.

The photographic illustration was taken when the fruit was firm ripe and during the 2nd harvest. The color described and represented are reasonably possible for this fruit type.

DETAILED DESCRIPTION OF NEW VARIETY

Dates of first and last pickings: September 17 and September 28.

Tree: Very large; Vigorous; Spreading and willowy; Moderately hardy, Productive, Regular bearer.

*Trunk.*—Medium.

*Branches.*—Medium. Lenticels — medium large.

*Leaves.*—Acutely pointed; medium, smooth. Length 6¼ inches to 6¾ inches. Width 1⅜ to 1½ inches. Color medium, glossy, green — Forrest Green Plate XVII 29M Ridgeway color standards. Form — lanceolate. Margin — crenate. Peteiole — medium long, medium thick. Glands — Reniform, number varies from 2 to 4, medium, opposite.

Flowers:

*Date of blossoms.*—April 15 — late.

*Size.*—Large, showy.

*Color.*—Pink.

*Pollen.*—Self fertile.

Fruit:

*Maturity when described.*—Firm ripe — September 18.

*Size.*—Variable, large to very large. Axial diameter — 2⅞ to 3⅛ inches. Transverse in suture plains — 3⅛ inches. At right angles to suture plains 3⅛ inches.

*Form.*—Uniform, unsymmetrical and globose to slightly ovate.

*Suture.*—Distinct, extends from base to apex. Raised on opposite side.

*Ventral surface.*—Rounded, slightly lipped on either side.

*Cavity.*—Rounded, generally circular. Depth — ½ inch. Breadth — ½ inch. Markings — none.

*Base.*—Retuse.

*Apex.*—Emarginate.

*Stem.*—Short length, pubescent, medium thick.

*Skin.*—Medium thick, free, pubescence slight. Color — highly blushed red 75 to 85% of surface, Peach Red 15b, Ridgeway color standards, and approximately 15 to 25% of mottled reddish yellow to green yellow undercolor on side not exposed to sun.

Flesh:

*Color.*—Golden yellow with red streaks radiating from pit.

*Surface of pit cavity.*—Red, occasional yellow streaks.

*Amygladin.*—Scant.

*Texture.*—Firm melting.

*Fibers.*—Fine.

*Ripens.*—Evenly.

*Flavor.*—Mild, sub acid.

*Aroma.*—Slight.

*Eating quality.*—Very good.

Stone:

*Fibers.*—Parts from flesh cleanly.

*Size.*—Large, length 1½ inches, thickness ⅞ inches.

*Form.*—Oval.

*Base.*—Oval.

*Apex.*—Acute.

*Sides.*—Mostly equal.

*Surface.*—Furrowed toward apex, pitted toward base.

*Use.*—Fresh market, dessert.

*Keeping quality.*—Excellent.

*Resistance to insects.*—Good.

*Resistance to diseases.*—Good.

*Shipping quality.*—Very good.

I claim:

1. A new and distinct variety of yellow freestone peach, substantially as illustrated and described, characterized by a strong, vigorous growth spreading habit, moderate tolerance to bacterial leaf spot, and the ability to yield very large, globose, very firm orange red colored, slow softening fruit having a very good subacid flavor which commonly ripens very late, 5 to 7 days after Autumnglo, Encore and Rio Oso Gem.

* * * * *